(12) United States Patent
Tippet et al.

(10) Patent No.: US 8,444,615 B2
(45) Date of Patent: May 21, 2013

(54) ONE-PIECE SUCTION CANISTER LINER

(75) Inventors: Jon Tippet, League City, TX (US); John Gaustad, Friendswood, TX (US); Steve Harden, Pasadena, TX (US); Leland Daniels, Dayton, TX (US)

(73) Assignee: Fina Technology, Inc., Houston, TX (US)

( * ) Notice: Subject to any disclaimer, the term of this patent is extended or adjusted under 35 U.S.C. 154(b) by 113 days.

(21) Appl. No.: 13/031,319

(22) Filed: Feb. 21, 2011

(65) Prior Publication Data
US 2012/0215187 A1  Aug. 23, 2012

(51) Int. Cl.
*A61M 1/00* (2006.01)
(52) U.S. Cl.
USPC .......................................................... 604/319
(58) Field of Classification Search
None
See application file for complete search history.

(56) References Cited

U.S. PATENT DOCUMENTS

| | | |
|---|---|---|
| 4,384,580 A | 5/1983 | Leviton |
| 4,430,084 A | 2/1984 | Deaton |
| 5,118,003 A | 6/1992 | Pepper et al. |
| 5,339,959 A | 8/1994 | Cornwell |
| 5,725,516 A | 3/1998 | Cook et al. |
| 7,674,248 B2 | 3/2010 | Anderson et al. |
| 7,806,879 B2 | 10/2010 | Brooks et al. |

OTHER PUBLICATIONS

Cardinal CRD Suction Liner Product Description [online], [retrieved on May 11, 2011]. Retrieved from the CardinalHealth web site using Internet <URL: http://www.cardinal.com/us/en/distributedproducts/ASP/65651-510.asp?cat=physician>.
Cardinal Guardian Suction Canisters Product Description [online], [retrieved on May 5, 2011]. Retrieved from the CardinalHealth web site using Internet <URL: http://www.cardinalhealth.com/us/en/distributedproducts/ASP/65651-212.asp?cat=med_surg-orig>.

*Primary Examiner* — Melanie Hand
*Assistant Examiner* — Joshua Lee

(57) ABSTRACT

A suction canister liner including a one-piece liner having a generally cylindrical shape with an open end, a closed end, a sidewall connecting the open end to the closed end, and a rim extending outward generally perpendicular to the sidewall at the open end. An inner surface of the sidewall at the open end of the liner is configured to receive a lid in a sealing engagement and the rim can engage an open-ended suction canister and support the liner within the suction canister.

25 Claims, 6 Drawing Sheets

ONE-PIECE SUCTION CANISTER LINER

FIELD

The present invention relates to a suction canister liner such as is commonly used in the medical field for collection of biological waste fluids associated with surgery. Specifically, the invention relates to a one-piece semi-rigid liner for use with a suction canister and lid.

BACKGROUND

Suction canisters are prevalent in the medical field for collection of biological fluids that may be infectious. These fluids may be collected during or after a surgical procedure. A major issue with suction canisters is the safe disposal of all the potentially infectious material, including the fluid and the fluid container. To minimize potential exposure of medical personnel to the canister contents, many facilities use a disposable liner. After use, the fluids and the liner may be disposed of in a manner that minimizes the infectivity potential of both. Potentially infectious fluids may be disposed of separately from the liner, which is frequently disposed of as red bag, or biohazard, waste due to its infectious potential. Alternatively, a solidifying agent may be added to solidify the fluid contents and enable the liner with its contents to be disposed with general waste.

A canister liner is placed inside a suction canister that protectively retains and isolates the liner from the environment to prevent rupture or spillage. A ring may secure either the lid to the liner, the liner to the canister, or both. Due to the high volume of suction canisters used in medical facilities and the desired disposability of the liners, suction canister liners are typically made from plastics. Whereas the suction canister is commonly made of a strong tough material such as polycarbonate, the liner, ring, and lid are typically made from less expensive and weaker materials.

Liners are frequently thermoformed plastic such as polypropylene (PP). The attachment ring and lid are frequently formed by injection molding polypropylene. To thermoform a liner, a plastic sheet can be heated before it is pressed and/or stretched into a mold. With injection molding, a molten polymer can be injected into a mold and allowed to cool. However, the polypropylene liner systems are known in the art to leak and experience chronic reflux while in operation when the vacuum pressure is removed. Furthermore, such a liner system requires the manufacture and assembly of three components: the liner, the ring, and the lid.

Thus, it is desirable for suction canister liners to have low cost, but be capable of withstanding the suction forces applied to them without leaking, reflux, or rupture. It is also desirable for economic reasons to reduce the time and material needed for manufacture of the liner system components.

SUMMARY OF THE INVENTION

The present invention generally relates to a one-piece semi-rigid liner for use with a suction canister.

In a non-limiting embodiment, either by itself or in combination with any other aspect of the invention, the present invention is a canister liner having a generally cylindrical shape with an open end, a closed end, a sidewall connecting the open end to the closed end and a rim extending outward generally perpendicular to the sidewall at the open end. An inner surface of the sidewall at the open end of the liner is configured to receive a lid in sealing engagement. The rim can engage an open-ended suction canister and support the liner within the suction canister. The liner can be made of a polymeric material selected from the group consisting of polypropylene (PP), acrylonitrile butadiene styrene (ABS), polyethylene terephthalate (PET), styrene acrylonitrile (SAN), polyvinyl chloride (PVC), general purpose polystyrene (GPPS), high impact polystyrene (HIPS), styrene-butadiene rubber (SBR), styrene block copolymer (SBC), and combinations thereof. The inner surface of the sidewall at the open end of the liner can include an undercut and can include a trap ring. The liner can have a diameter that decreases from the open end to the closed end and is configured to fit inside a suction canister and to nest with other similarly sized liners.

The liner can have a sidewall thickness of less than 0.018 inches and a sidewall deflection of less than 0.05 inches when subjected to a vacuum pressure of 29" Hg, optionally the liner has a sidewall thickness of 0.016 inches or less and a sidewall deflection of less than 0.05 inches when subjected to a vacuum pressure of 29" Hg. The sidewall can deflect less than 300% the sidewall thickness when subjected to a vacuum pressure of about 29" Hg. The liner can have a volumetric capacity from 1000 to 5000 cc.

In a non-limiting embodiment, either by itself or in combination with any other aspect of the invention, the present invention is an apparatus that includes a suction canister having a generally cylindrical shape with an open end. The apparatus also includes a one-piece liner having a generally cylindrical shape with an open end, a closed end, a sidewall connecting the open end to the closed end and a rim extending outwardly at the open end. The apparatus also includes a lid having a plurality of ports. The inner surface of the sidewall at the open end of the liner can be configured to receive the lid in a sealing engagement. The liner can fit inside the suction canister and the liner rim can engage the open end of the suction canister and support the liner within the suction canister.

DETAILED DESCRIPTION

The present invention generally relates to a leak resistant semi-rigid one-piece ring-liner assembly to use with a suction canister system.

Figure 1:
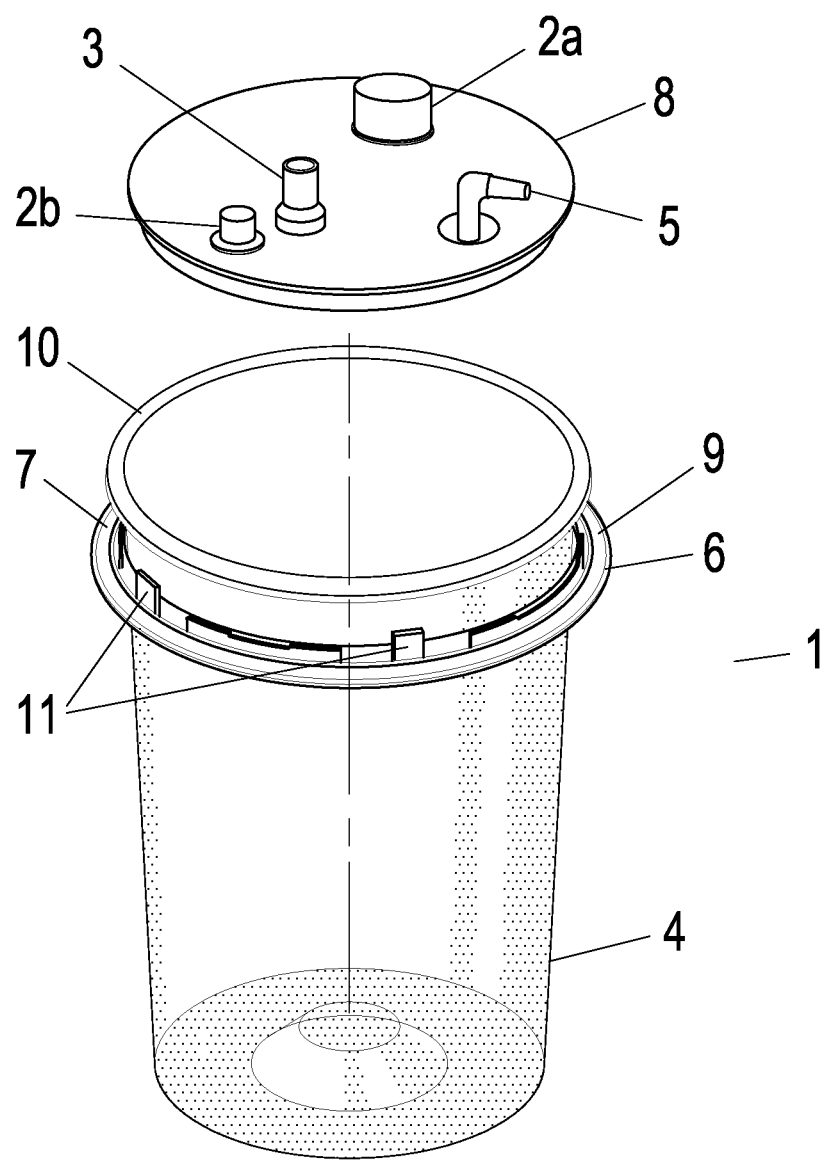
FIG. 1 illustrates a medical apparatus of the prior art for retaining biological fluids suctioned from a patient wound site.

FIG. 1 depicts the component parts of a prior art suction containment apparatus. As shown in FIG. 1, a suction apparatus 1 includes a liner 4, a ring 6, and a lid 8. The ring 6 is designed to engage the lip 10 of the liner 4. The ring 6 contains a groove 9 on the topside 7 of the ring 6 that is designed to receive the underside of lip 10 of the liner 4. The ring 6 is also designed to engage the lid 8 so as to create a seal between the lid 8 and the liner 4. The ring 6 contains clips 11, which are designed to engage the lid 8 and hold it in place.

When the lid 8 is clipped into place via the clips 11, a seal is created between the lid 8 and the liner 4. The liner 4 may contain optional markings (not shown) to indicate the approximate volume within the liner 4. The lid 8 may be an elastomer or an injection molded plastic such as polypropylene. The lid 8 can have an inlet port 3 configured to receive fluids from a patient wound site (not shown) as liner contents (not shown). The lid 8 can also have a vacuum port 5 configured to connect to a vacuum source (not shown). The vacuum source may be a portable self-contained system or a fully integrated facility system as found in some medical facilities. The vacuum source applies vacuum pressure through the vacuum port 5, which pulls the fluids through the inlet port 3 into the liner 4. At least one access port 2a on the lid 8 can be configured to connect to a variety of suction canister accessories such as but not limited to another canister, a solidifying agent, or a post to store caps or plugs for the other ports. The lid 8 may also contain an auxiliary port 2b. The vacuum port 5, inlet port 3, at least one access port 2a, and an auxiliary port 2b may each be configured to engage a plug or cap (not shown) to seal the liner contents from the ambient air.

Figure 2:
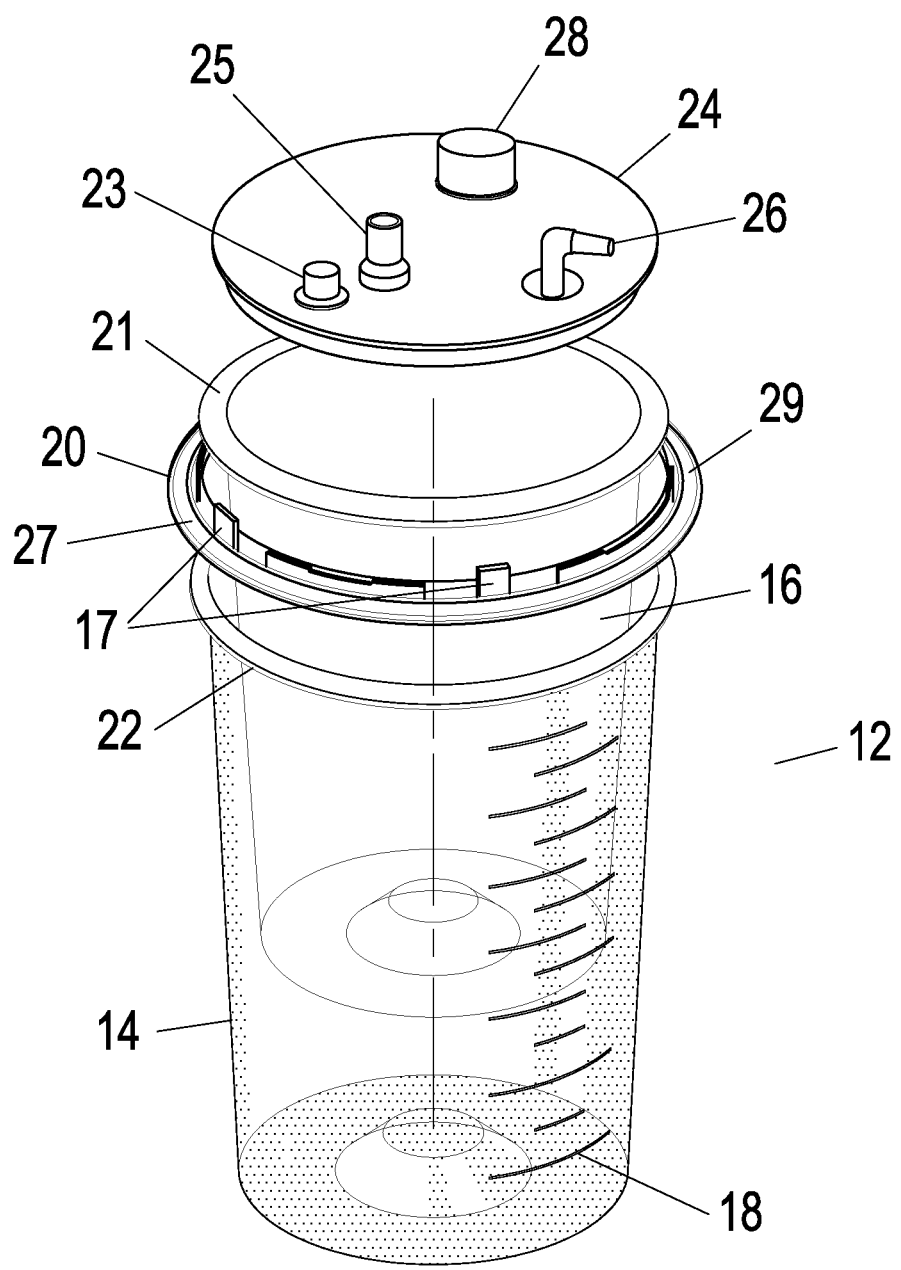
FIG. 2 illustrates another embodiment of the medical apparatus of the prior art.

FIG. 2 depicts a prior art suction canister apparatus. As shown in FIG. 2, a suction canister apparatus 12 includes a suction canister 14 and a liner 16. Both the canister 14 and the liner 16 are substantially cylindrical with a closed end and an open end. The canister 14 is configured to enable the liner 16 to fit inside the canister 14 such that the open liner end 16 is opposite the closed canister end. The suction canister 14 is desirably a rigid and transparent or translucent material, including but not limited to glass or polycarbonate. The suction canister 14 may have markings 18 to indicate the approximate volume within the liner 16. The liner 16 is connected to, or otherwise engaged with, a ring 20. The ring 20 contains a groove 29 on the topside 27 of the ring 20 that is designed to receive the underside of lip 21 of the liner 16. The groove 29 is capable of creating a seal between the underside of lip 21 and the ring 20. The suction canister 14 has a rim 22 that is configured to removably engage with the ring 20. The ring 20 may engage the suction canister 14 by means of wholly or partially enclosing part of the suction canister 14. A lid 24 may engage the ring 20 by means of clips 17 that are attached to, or integral with, the ring 20. Upon application of sufficient force, the clips 17 can cause the lid 24 to attach to the ring 20 and liner 16 by locking into, or by creating any other frictional bind with, a corresponding space (not shown) in the lid 24. When the lid 24 is clipped into place via the clips 17, a seal is created between the lid 24 and the liner 16. The enclosed suction canister apparatus includes a seal created between the lid 24 and lip 21 and a separated seal created between the underside of lip 21 and the ring 20, wherein the ring 20 is engaged with the rim 22 of canister 14, resulting in an enclosed suction canister apparatus capable of collecting fluid(s) via a vacuum. The lid 24 may be an elastomer or an injection molded plastic such as polypropylene. The lid 24 can have an inlet port 25 configured to receive fluids from a patient wound site (not shown) as liner contents (not shown). The lid 24 can also have a vacuum port 26 configured to connect to a vacuum source (not shown). The vacuum source may be a portable self-contained system or a fully integrated facility system as found in some medical facilities. The vacuum source applies vacuum pressure through the vacuum port 26, which pulls the fluids through the inlet port 25 into the liner 16. At least one access port 28 on the lid 24 can be configured to connect to a variety of suction canister accessories such as but not limited to another canister, a solidifying agent, or a post to store caps or plugs for the other ports. The lid 24 may also contain an auxiliary port 23. The vacuum port 26, inlet port 25, at least one access port 28, and an auxiliary port 23 may each be configured to engage a plug or cap (not shown) to seal the liner contents from the ambient air.

Figure 3:
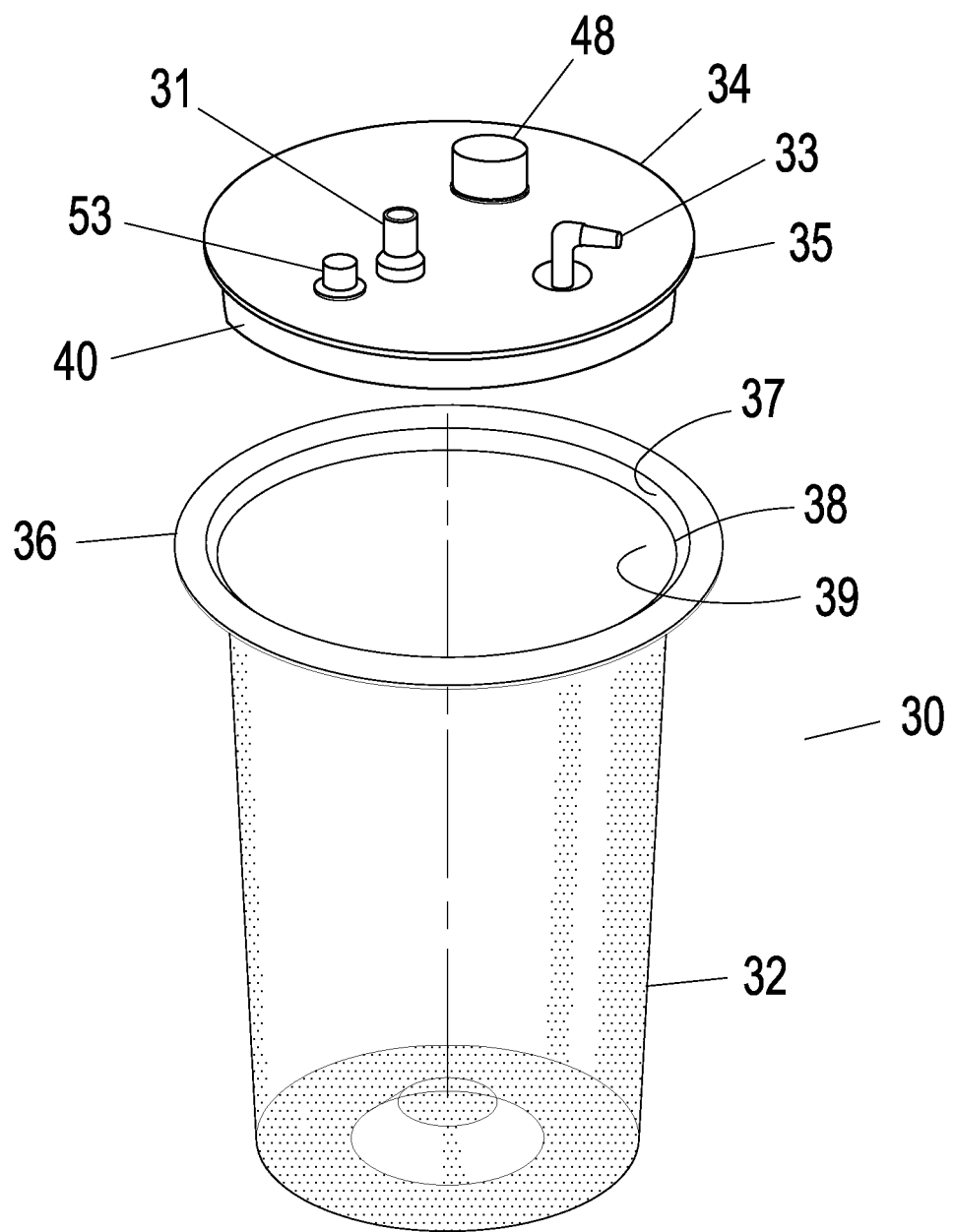
FIG. 3 illustrates an embodiment of a medical apparatus of the present invention for retaining biological fluids suctioned from a patient wound site.

An embodiment of the present invention is depicted in FIG. 3. As shown in FIG. 3, a suction containment apparatus 30 includes a liner 32 and a lid 34. The lid 34 has an outer edge 35. The liner 32 has a lip section 36 with an inner surface 37 designed to engage the outer edge 35 of the lid 34 so as to create a continuous 360-degree seal between the lid 34 and liner 32. The seal of the present invention is advantageous over the prior art seal because the prior art seal relies on specific pressure points from the clips that hold the seal together, whereas the liner 32 of the present invention is capable of creating a continuous seal under a constant evenly distributed pressure around the circumference of the lid 34. The inner surface 37 can include an optional undercut, recess, taper, groove, or other configuration (collectively referred to herein as an undercut) integral with the liner 32. The undercut can have a shape such that if serves as a trap ring when the lid is engaged into the inner surface 37 that forms a seal between the liner 32 and the inner surface 37 and effectively secures the lid 34 within the inner surface 37 of the liner 32. The lid 34 includes a lower portion 40 that inserts into the liner 32 and can engage a second inner surface 39 of the liner 32, which can create a second seal between the lid 34 and liner 32, that can be a continuous 360-degree seal. The lip section 36 can include a rolled lip such that the edge of the lip section 36 is smooth. The rolled lip can provide added strength to the liner 32 compared to a flat/non-rolled lip section. Optionally, the liner 32 may contain markings (not shown) to indicate the approximate volume within the liner 32.

The lid 34 may be an elastomer or an injection molded plastic such as polypropylene. The lid 34 can have an inlet port 31 configured to receive fluids from a patient wound site (not shown) as liner contents (not shown). The lid 34 can also have a vacuum port 33 configured to connect to a vacuum source (not shown). The vacuum source may be a portable self-contained system or a fully integrated facility system as found in some medical facilities. The vacuum source applies vacuum pressure through the vacuum port 33, which pulls the fluids through the inlet port 31 into the liner 32. The vacuum port 33 can have an integrated filter, shut-off valve, or other mechanism (not shown) to prevent the liner contents from leaving the liner 32 while permitting filtered air passage to the vacuum source. At least one access port 48 on the lid 34 can be configured to connect to a variety of suction canister accessories such as but not limited to another canister, a solidifying agent, or a post to store caps or plugs for the other ports. The lid 34 may also contain an auxiliary port 53. The vacuum port 33, inlet port 31, at least one access port 48, and an auxiliary port 53 may each be configured to engage a plug or cap (not shown) to seal the liner contents from the ambient air.

The liner 32 may contain an undercut (not shown), such as a taper or recess on its inner surface 37 to serve the function of a ring in the prior art as illustrated in FIG. 1 rather than a separate component that is subsequently attached to the liner 32. The inner surface 37 is integral to the liner 32 and configured to receive and engage a lid 34 to seal the liner contents from the ambient air. In an embodiment, the lid 34 has a lower portion 40 that is a smooth tapered section that engages and creates a friction seal with the second inner surface 39 of the liner 32. The inner surface 37 of the liner 32 can have a larger diameter than the second inner surface 39 of the liner 32, enabling the outer edge 35 of the lid 34 to engage the inner surface 37 of the liner 32 while also enabling the lower portion 40 of the lid 34 to engage the second inner surface 39 of the liner 32. The transition edge 38 from the inner surface 37 of the liner 32 to the second inner surface 39 of the liner 32 can function as a barrier that prevents the outer edge 35 of the lid 34 from entering within the second inner surface 39 of the liner 32. In an embodiment, both the lid 34 and the liner 32 have a threaded means for attaching and forming a seal.

Figure 4:
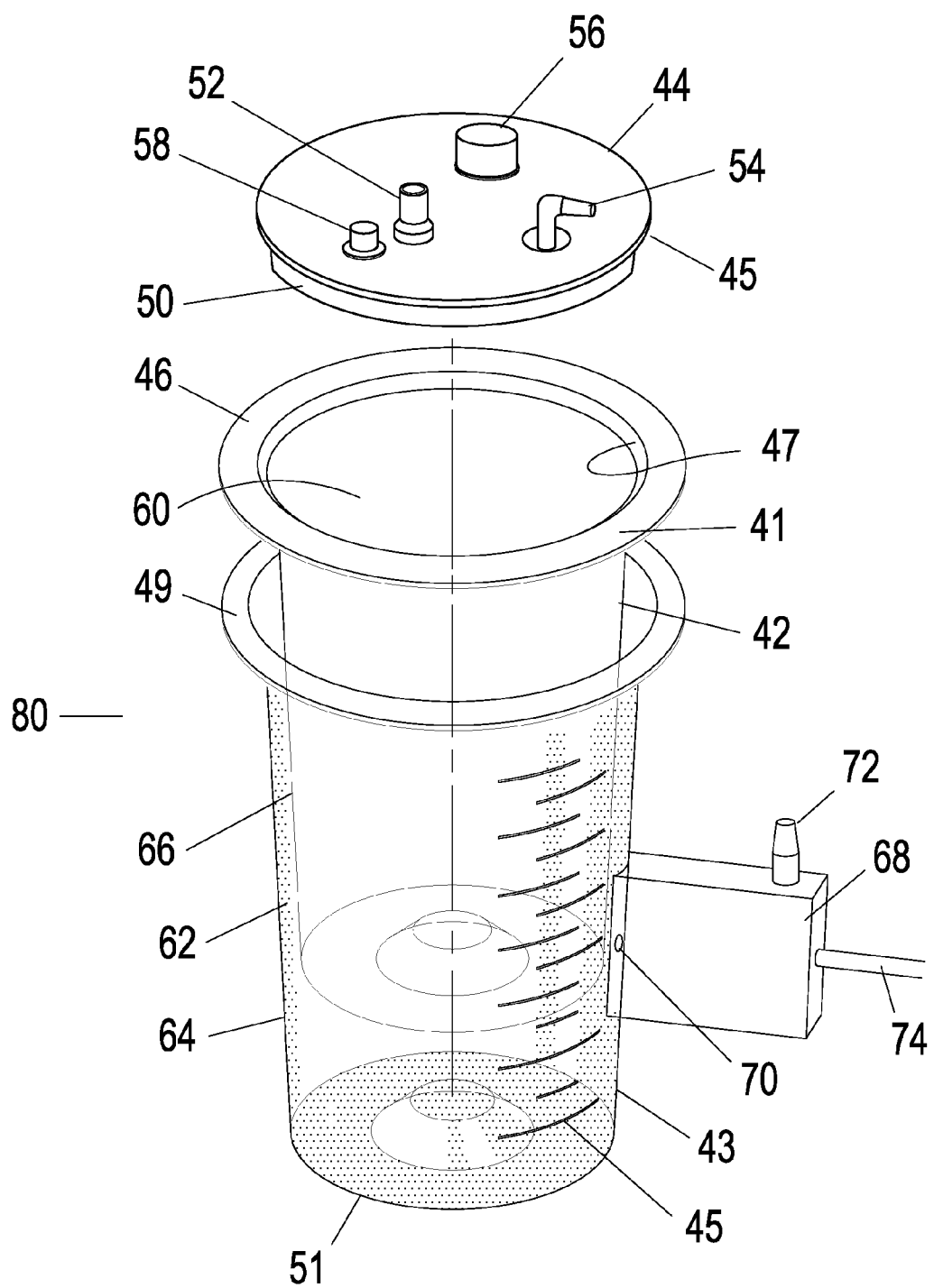
FIG. 4 illustrates another embodiment of the medical apparatus of the present invention having an outer container.

An embodiment of the present invention is depicted in FIG. 4. As shown in FIG. 4, a suction canister apparatus 80 includes a liner 42, a canister 43, and a lid 44. Both the canister 43 and the liner 42 are substantially cylindrical with a closed end and an open end. The canister 43 is configured to enable the liner 42 to fit inside the canister 43 such that the open liner end 41 is opposite the closed canister end 51. The canister 43 may be constructed from a rigid and transparent or translucent material, including but not limited to glass or polycarbonate. The suction canister 43 may have markings 45 to indicate the approximate volume within the liner 42. The suction canister 43 has a canister rim 49 that is configured to removably engage with a liner rim 46. The liner rim 46 may engage the suction canister 43 by means of wholly or partially enclosing part of the suction canister 43. The lid 44 has an outer edge 45 designed to engage an inner surface 47 of the liner 42 so as to create a seal between the lid 44 and liner 42. The lid 44 can also have a lower portion 50 designed to engage a second inner surface 48 of the liner 42 so as to create another seal between the lid 44 and liner 42.

The lid 44 may be an elastomer or an injection molded plastic such as polypropylene. The lid 44 can have an inlet port 52 configured to receive fluids from a patient wound site (not shown) as liner contents (not shown). The lid 44 can also have a vacuum port 54 configured to connect to a vacuum source (not shown). The vacuum source may be a portable self-contained system or a fully integrated facility system as found in some medical facilities. The vacuum source applies vacuum pressure through the vacuum port 54, which pulls the fluids through the inlet port 52 into the liner containment space 60. The vacuum port 54 can have an integrated filter, shut-off valve, or other mechanism (not shown) to prevent the liner contents from leaving the containment space 60 while permitting filtered air passage to the vacuum source. At least one access port 56 on the lid 44 can be configured to connect to a variety of suction canister accessories such as but not limited to another canister, a solidifying agent, or a post to store caps or plugs for the other ports. The lid 44 may also contain an auxiliary port 58. The vacuum port 54, inlet port 52, at least one accessory port 56, and an auxiliary port 58 may each be configured to engage a plug or cap (not shown) to seal the liner contents from the ambient air.

Placing the liner 42 within the canister 43 forms a cavity 62 between the suction canister sidewall 64 and the liner wall 66. Attaching the liner rim 46 to the canister rim 49 can at least partially seal the cavity 62 from the ambient air. In an embodiment, a vacuum is applied to this cavity 62 through a port 70 in the canister wall. A mounting bracket 68 can be attached to the canister 43 for use in mounting the canister 43 to a wall or a stand (not shown). The mounting bracket 68 can include a vacuum conduit 74 that connects to a suction source (not shown) and can include attachment to the port 70 for applying vacuum to the cavity 62. The mounting bracket 68 can include a suction port 72 that can be connected to the vacuum port 54 to provide suction within the liner 42.

The liner 42 can be a semi-rigid material capable of retaining its structural integrity during and after repeated subjection to vacuum pressures up to or greater than 29" Hg (98.2 kPa). The liner 42 can be disposable, thus it may be made of any inexpensive or otherwise disposable material. In an embodiment, the liner 42 is formed from a polymeric material. In another embodiment, the liner 42 is formed from a material selected from acrylonitrile butadiene styrene (ABS), polyethylene terephthalate (PET), styrene acrylonitrile (SAN), polyvinyl chloride (PVC), styrene-butadiene rubber (SBR), styrene block copolymer (SBC), styrenic copolymers, polypropylene (PP), polycarbonate (PC), polystyrene (PS), general purpose polystyrene (GPPS), or high impact polystyrene (HIPS). In an embodiment, a first liner is formed from HIPS, wherein the first liner deflects less upon being subjected to a vacuum source under operation when compared to a second liner formed from polypropylene but having the same size and dimensions as the first liner. In a non-limiting embodiment, either by itself or in combination with any other aspect of the invention, the first liner formed from HIPS deflects at least 20% less, optionally at least 30% less, optionally at least 40% less, optionally at least 50% less, than a second liner formed from polypropylene having the same size and dimensions as the first liner when subjected to a vacuum pressure of 29" Hg.

The liner 42 can have any desired thickness. In an embodiment, the liner has a sidewall thickness ranging from 0.001 to 0.100 inches. In another embodiment, the liner has a sidewall thickness ranging from 0.005 to 0.050 inches. In a further embodiment, the liner has a sidewall thickness ranging from 0.010 to 0.025 inches, optionally from 0.012 to 0.020 inches, optionally from 0.014 to 0.018 inches, optionally from 0.015 to 0.017 inches. In an embodiment, the liner has a sidewall thickness of less than 0.018 inches, optionally less than 0.017 inches, optionally less than 0.016 inches, optionally less than 0.015 inches.

Upon the filling of the canister with material such as medical waste, the canister can be hermetically sealed for transport to disposal or a lab. In an embodiment, there is no communication between the containment space and the cavity between the liner and the canister.

The suction canister apparatus of the present invention may be of any desired size or dimension. In an embodiment the suction canister apparatus of the present invention may be of any typical size of suction canisters commonly in use. In an embodiment the suction canister apparatus of the present invention may range from 500 to 10,000 cc in fluid volume, optionally from 1000 to 5000 cc in fluid volume, optionally from 1200 to 3000 cc in fluid volume. In an embodiment the suction canister apparatus of the present invention may have a height ranging from 3 to 12 inches, optionally 4 to 10 inches, and optionally 5 to 8 inches. In an embodiment, the suction canister apparatus of the present invention may have a diameter ranging from 2 to 10 inches, optionally, 3 to 7 inches, and optionally 3 to 5 inches.

In an embodiment as illustrated in FIG. 4, the vacuum source applies a vacuum pressure to both the cavity 62 and the containment space 60. In an embodiment, the vacuum source applies a vacuum pressure of up to 29" Hg (98.2 kPa) to both the cavity 62 and the containment space 60. This vacuum pressure may be initially applied to the cavity 62 in order to form a seal between the suction canister 34 and the liner 42. The vacuum pressure applied to the cavity 62 is sealed and can cause the liner 42 to deflect outward toward the suction canister 43. The vacuum source can also apply vacuum pressure to the containment space 60 through the vacuum port 54 by means of a connection hose (not shown) between suction port 72 and vacuum port 54 and provides suction through the inlet port 52 to be used for the operation of fluid containment. As the containment space 60 is not sealed but open to the atmosphere through the inlet port 52, the pressure of the containment space 60 may be higher than the pressure in the cavity 62, thus causing the liner 42 to deflect outward toward the suction canister 43. Upon removal of the vacuum pressure from both the cavity 62 and the liner 42, the liner 42 may resume its original shape and volume, which may force fluid contents from the containment space 60 to rise in the liner 42 and lead to refluxing or leakage of the contents. In an embodiment, the liner 42 of the present embodiment is of adequate strength and rigidity to prevent the fluid contents from refluxing or leaking through the lid 44 when the vacuum pressure is removed while the liner 42 is full. In an embodiment, the volume decrease of the liner 42 and pressure increase of the contents are inadequate to force any of the liner contents out of the lid 44 by seal leakage or port reflux. As a non-limiting example, for a liner sidewall thickness of 0.015 inches, a deflection of 0.045 inches or less under a vacuum pressure of 29" Hg (98.2 kPa) would not force the liner contents out of the lid 44.

In another embodiment, the open end 41 of the liner 42 has a larger diameter than the canister rim 49, which has a larger diameter than the closed bottom end 51. The sidewalls 64 and 66 have a narrowing diameter between the open liner end 41, canister rim 49, and bottom canister end 51. The liner shape is such that one liner may nest at least partly inside another liner. This nesting property enables more compact liner packaging, transportation, and storage.

The liner of the present invention may have a stiffness or rigidity that is measured by the deflection of the sidewall of the liner when a vacuum load of 29" Hg (98.2 kPa) is applied to the exterior of the liner. In an embodiment, the liner has a sidewall thickness of 0.018 inches or less and a sidewall deflection of less than 0.05 inches, optionally less than 0.04 inches, optionally less than 0.03 inches. In a further embodiment, the liner has a sidewall thickness of 0.017 inches or less and a sidewall deflection of less than 0.05 inches, optionally less than 0.04 inches, optionally less than 0.03 inches. In a further embodiment, the liner has a sidewall thickness of 0.016 inches or less and a sidewall deflection of less than 0.06 inches, optionally less than 0.05 inches, optionally less than 0.04 inches. In a further embodiment, the liner has a sidewall thickness of 0.015 inches or less and a sidewall deflection less than 0.06 inches, optionally less than 0.05 inches, optionally less than 0.045 inches. In a further embodiment, the liner has a sidewall thickness of 0.014 inches or less and a sidewall deflection less than 0.06 inches, optionally less than 0.05 inches. In a further embodiment, the liner has a sidewall thickness of 0.013 inches or less and a sidewall deflection less than 0.075 inches, optionally less than 0.06 inches.

EXAMPLES

Comparative liners were produced from high impact polystyrene (HIPS) and polypropylene. The HIPS used was 940E commercially available from Total Petrochemicals, Inc. The polypropylene used was 9231 PP commercially available from Huntsman Corporation. The HIPS liners thermoformed 35% faster than the PP liners under the same process. The resulting HIPS liners were tested in a four hour vacuum test that subjected the liners to a minimum vacuum of 20" Hg (67.7 kPa) for 15 second cycles. The HIPS liners passed the vacuum cycle testing.

A Finite Element Analysis (FEA) model was used to compare the deflection due to vacuum pressure for liners made from the PP and HIPS. The models varied the liner thickness to determine modeled deflection values for each material under vacuum pressure. In each model, a vacuum load of 29" Hg (98.2 kPa, 14.24 psi) was placed on the outside of the liner and partially the closed end. The load was only applied to the exterior of the liner in order to evaluate an initial deflection due to operating conditions because a vacuum may be applied on the outside of the liner initially through the cavity between the liner and canister, prior to a vacuum being applied to the inside of the liner for use as a suction.

Figure 5:
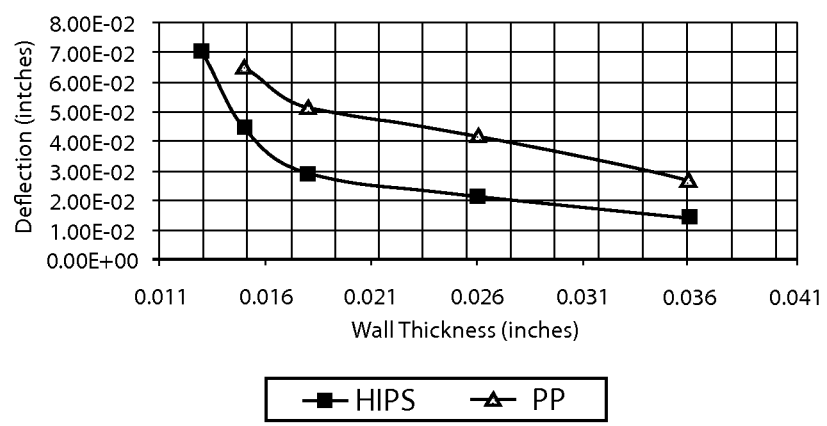
FIG. 5 shows a graph of modeled deformation under vacuum for varying thickness liners made from PP and HIPS.

The FEA results indicate that for all wall thicknesses modeled, the HIPS liners provided a significant reduction in wall deflection compared to the liners made from PP. The deflection for the PP and HIPS and the percentage reduction in deflection for HIPS liners compared to the PP liners for each modeled thickness is shown in Table 1 and FIG. 5. The sidewall of the modeled HIPS deflects from about 30% to 50% less under the simulated vacuum load than the PP.

TABLE 1

Modeled deflection for PP and HIPS liners at 29" Hg.

| Material | Thickness (in) | Deflection (in) | Deflection/Thickness | % reduction |
|---|---|---|---|---|
| PP | 0.015 | 6.50E−02 | 434% | |
| PP | 0.018 | 5.13E−02 | 285% | |
| PP | 0.026 | 4.13E−02 | 159% | |
| PP | 0.036 | 2.62E−02 | 73% | |
| HIPS | 0.013 | 7.06E−02 | 543% | |
| HIPS | 0.015 | 4.45E−02 | 297% | 32% |
| HIPS | 0.018 | 2.87E−02 | 159% | 44% |
| HIPS | 0.026 | 2.07E−02 | 79% | 50% |
| HIPS | 0.036 | 1.32E−02 | 37% | 50% |

Figure 6:
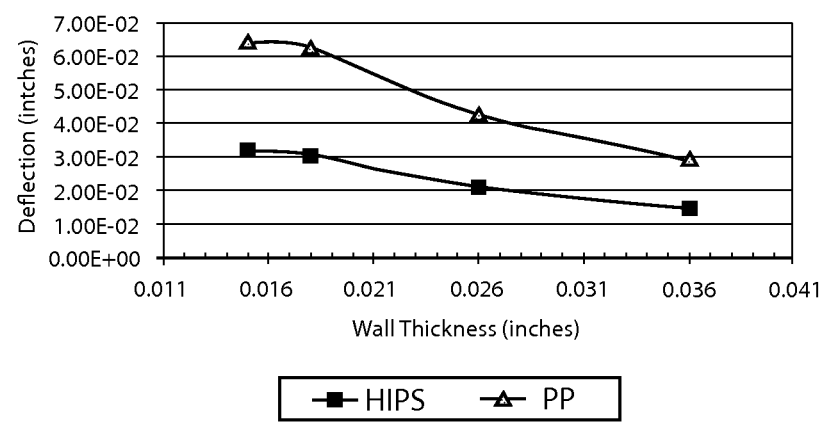
FIG. 6 shows a graph of modeled deformation under vacuum for varying thickness liners of PP and HIPS.

Another FEA model applying the vacuum load of 29" Hg (98.2 kPa, 14.24 psi) on only the sidewall of the liner also indicated that a HIPS liner deflects less than a PP liner of equal thickness. The sidewall of the modeled HIPS deflects about 50% less under the vacuum load than the PP as shown in Table 2 and FIG. 6.

TABLE 2

Modeled sidewall deflection comparison for PP and HIPS liners

| Material | Thickness (in) | Deflection (in) | Deflection/Thickness | % reduction |
|---|---|---|---|---|
| PP | 0.015 | 6.41E−02 | 427% | — |
| PP | 0.018 | 6.23E−02 | 346% | — |
| PP | 0.026 | 4.22E−02 | 162% | — |
| PP | 0.036 | 2.87E−02 | 80% | — |
| HIPS | 0.015 | 3.21E−02 | 214% | 50% |
| HIPS | 0.018 | 3.02E−02 | 168% | 51% |
| HIPS | 0.026 | 2.07E−02 | 79% | 51% |
| HIPS | 0.036 | 1.41E−02 | 39% | 51% |

Various terms are used herein, to the extent a term used is not defined herein, it should be given the broadest definition persons in the pertinent art have given that term as reflected in printed publications and issued patents. Various ranges are further recited herein. It should be recognized that unless stated otherwise, it is intended that the endpoints are to be interchangeable. Further, any point within that range is contemplated as being disclosed herein Use of broader terms such as comprises, includes, having, etc. should be understood to provide support for narrower terms such as consisting of, consisting essentially of, comprised substantially of, etc.

Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

It is to be understood that while illustrative embodiments have been depicted and described, modifications thereof can be made by one skilled in the art without departing from the spirit and scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.).

Depending on the context, all references herein to the "invention" may in some cases refer to certain specific embodiments only. In other cases it may refer to subject matter recited in one or more, but not necessarily all, of the claims. While the foregoing is directed to embodiments, versions and examples of the present invention, which are included to enable a person of ordinary skill in the art to make and use the inventions when the information in this patent is combined with available information and technology, the inventions are not limited to only these particular embodiments, versions and examples. Also, it is within the scope of this disclosure that the aspects and embodiments disclosed herein are usable and combinable with every other embodiment and/or aspect disclosed herein, and consequently, this disclosure is enabling for any and all combinations of the embodiments and/or aspects disclosed herein. Other and further embodiments, versions and examples of the invention may be devised without departing from the basic scope thereof and the scope thereof is determined by the claims that follow.

The invention claimed is:

1. A suction canister liner comprising:
a one-piece liner having a generally cylindrical shape with an open end, a closed end, a sidewall connecting the open end to the closed end, and a rim extending outward generally perpendicular to the sidewall at the open end;
wherein an inner surface of the sidewall at the open end of the liner is configured to receive a lid in sealing engagement;
wherein the rim can engage an open-ended suction canister and support the liner within the suction canister, wherein the liner has a sidewall thickness of less than 0.018 inches and a sidewall deflection of less than 0.05 inches when subjected to a vacuum pressure of 29" Hg.

2. The liner of claim 1, wherein the liner is made of a polymeric material selected from the group consisting of PP, ABS, PET, SAN, PVC, GPPS, HIPS, SBR, SBC, and combinations thereof.

3. The liner of claim 1, wherein the polymeric material is HIPS.

4. The liner of claim 1, wherein the liner has a radius that decreases from the open end to the closed end and is configured to fit inside a suction canister and to nest with other similarly sized liners.

5. The liner of claim 1, wherein the liner has a volumetric capacity from 1000 to 5000 cc.

6. A suction canister liner comprising:
a one-piece liner having a generally cylindrical shape with an open end, a closed end, a sidewall connecting the open end to the closed end, and a rim extending outward generally perpendicular to the sidewall at the open end;
wherein an inner surface of the sidewall at the open end of the liner is configured to receive a lid in sealing engagement;
wherein the rim can engage an open-ended suction canister and support the liner within the suction canister, wherein the liner has a sidewall thickness of 0.016 inches or less and a sidewall deflection of less than 0.05 inches when subjected to a vacuum pressure of 29" Hg.

7. A suction canister liner comprising:
a one-piece liner having a generally cylindrical shape with an open end, a closed end, a sidewall connecting the open end to the closed end, and a rim extending outward generally perpendicular to the sidewall at the open end;
wherein an inner surface of the sidewall at the open end of the liner is configured to receive a lid in sealing engagement;
wherein the rim can engage an open-ended suction canister and support the liner within the suction canister, wherein the sidewall deflects less than 300% the sidewall thickness when subjected to a vacuum pressure of about 29" Hg.

8. The liner of claim 7, wherein the liner is made of a polymeric material selected from the group consisting of PP, ABS, PET, SAN, PVC, GPPS, HIPS, SBR, SBC, and combinations thereof.

9. The liner of claim 7, wherein the polymeric material is HIPS.

10. The liner of claim 7, wherein the liner has a radius that decreases from the open end to the closed end and is configured to fit inside a suction canister and to nest with other similarly sized liners.

11. The liner of claim 7, wherein the liner has a volumetric capacity from 1000 to 5000 cc.

12. A suction canister apparatus comprising:
a suction canister having a generally cylindrical shape with an open end;
a one-piece liner having a generally cylindrical shape with an open end, a closed end, a sidewall connecting the open end to the closed end, and a rim extending outwardly at the open end; and
a lid having a plurality of ports;
wherein an inner surface of the sidewall at the open end of the liner is configured to receive the lid in sealing engagement;
wherein the liner can fit inside the suction canister and the liner rim can engage the open end of the suction canister and support the liner within the suction canister, wherein the sidewall deflects less than 300% the sidewall thickness when subjected to a vacuum pressure of about 29" Hg.

13. The apparatus of claim 12, wherein the liner is made of a polymeric material selected from the group consisting of PP, ABS, PET, SAN, PVC, GPPS, HIPS, SBR, SBC, and combinations thereof.

14. The apparatus of claim 13, wherein the polymeric material is HIPS.

15. The apparatus of claim 12, wherein the liner and lid seal is a continuous friction seal along the inner surface of the sidewall at the open end of the liner.

16. The apparatus of claim 12, wherein the liner has a radius that decreases from the open end to the closed end and is configured to fit inside a suction canister and to nest with other similarly sized liners.

17. The apparatus of claim 16, wherein the sidewall deflection of the liner is less than 0.05 inches when subjected to a vacuum pressure of 29" Hg.

18. The apparatus of claim 12, wherein the liner has a volumetric capacity from 1000 to 5000 cc.

19. A suction canister apparatus comprising:
a suction canister having a generally cylindrical shape with an open end;
a one-piece liner having a generally cylindrical shape with an open end, a closed end, a sidewall connecting the open end to the closed end, and a rim extending outwardly at the open end; and a lid having a plurality of ports;

wherein an inner surface of the sidewall at the open end of the liner is configured to receive the lid in sealing engagement;

wherein the liner can fit inside the suction canister and the liner rim can engage the open end of the suction canister and support the liner within the suction canister, wherein the liner has a sidewall thickness of less than 0.018 inches and a sidewall deflection of less than 0.05 inches when subjected to a vacuum pressure of 29" Hg.

20. The apparatus of claim 19, wherein the liner is made of a polymeric material selected from the group consisting of PP, ABS, PET, SAN, PVC, GPPS, HIPS, SBR, SBC, and combinations thereof.

21. The apparatus of claim 20, wherein the polymeric material is HIPS.

22. The apparatus of claim 19, wherein the liner and lid seal is a continuous friction seal along the inner surface of the sidewall at the open end of the liner.

23. The apparatus of claim 19, wherein the liner has a radius that decreases from the open end to the closed end and is configured to fit inside a suction canister and to nest with other similarly sized liners.

24. The apparatus of claim 19, wherein the liner has a volumetric capacity from 1000 to 5000 cc.

25. A suction canister apparatus comprising:

a suction canister having a generally cylindrical shape with an open end;

a one-piece liner having a generally cylindrical shape with an open end, a closed end, a sidewall connecting the open end to the closed end, and a rim extending outwardly at the open end; and a lid having a plurality of ports;

wherein an inner surface of the sidewall at the open end of the liner is configured to receive the lid in sealing engagement;

wherein the liner can fit inside the suction canister and the liner rim can engage the open end of the suction canister and support the liner within the suction canister, wherein the liner has a sidewall thickness of less than 0.016 inches and a sidewall deflection of less than 0.05 inches when subjected to a vacuum pressure of 29" Hg.

* * * * *